United States Patent [19]

Hubbard et al.

[11] Patent Number: 4,787,381
[45] Date of Patent: Nov. 29, 1988

[54] ABDOMINAL BINDER

[75] Inventors: Vance M. Hubbard, Bedford; Welton K. Brunson, both of Bedford, Tex.

[73] Assignee: Tecnol, Inc., Fort Worth, Tex.

[21] Appl. No.: 820,000

[22] Filed: Jan. 21, 1986

[51] Int. Cl.⁴ .............................................. A61F 5/04
[52] U.S. Cl. .................................. 128/157; 128/156; 139/421
[58] Field of Search ................. 128/155, 156, 96.1, 128/100.1, 101.1, 134, 165, 157; 139/421, 422

[56] References Cited

U.S. PATENT DOCUMENTS

| | | | |
|---|---|---|---|
| 84,255 | 11/1868 | Brown | 128/169 |
| 519,727 | 5/1894 | Moore | 139/421 |
| 2,015,255 | 9/1935 | Charpier et al. | 128/156 |
| 2,096,564 | 10/1937 | Scholl | 128/156 |
| 2,164,360 | 7/1939 | Burkart | 128/155 X |
| 3,194,234 | 7/1965 | Duckman et al. | 128/155 X |
| 3,221,736 | 12/1965 | Heitzmann | 139/421 |
| 3,307,546 | 3/1967 | Cherio et al. | 128/157 |
| 3,396,406 | 8/1968 | Gongwer | 128/155 X |
| 3,509,875 | 5/1970 | Richter | 128/155 X |
| 3,529,601 | 9/1970 | Kirkland | 128/155 X |
| 3,561,436 | 2/1971 | Gaylord, Jr. | 128/157 |
| 3,578,773 | 5/1971 | Schultz | 128/96.1 |
| 3,724,457 | 4/1973 | Klatte | 128/157 |
| 3,949,742 | 4/1976 | Nowakowski | 128/155 |
| 4,084,586 | 4/1978 | Hettick | 128/165 |
| 4,207,885 | 6/1980 | Hampton et al. | 128/156 |
| 4,505,271 | 3/1985 | Weber | 128/165 |
| 4,556,055 | 12/1985 | Bonner, Jr. | 128/82.1 |

Primary Examiner—Gregory E. McNeill
Assistant Examiner—J. Welsh
Attorney, Agent, or Firm—Jerry W. Mills; Jefferson Perkins; A. Bruce Clay

[57] ABSTRACT

Disclosed is a body wrap (10) securable around the waist (12) of a person (14). The body wrap (10) includes a unidirectionally stretchable panel (16) integral at one side edge thereof with a hook-like fastening section (24), and integral at the other side edge thereof with a large brushed pile material section (28). The unidirectionally stretchable panel (16) is constructed of plural elongate stretchable support sections (22) alternating between plural apertured sections (18) through which a sutured incision may be observed.

8 Claims, 2 Drawing Sheets

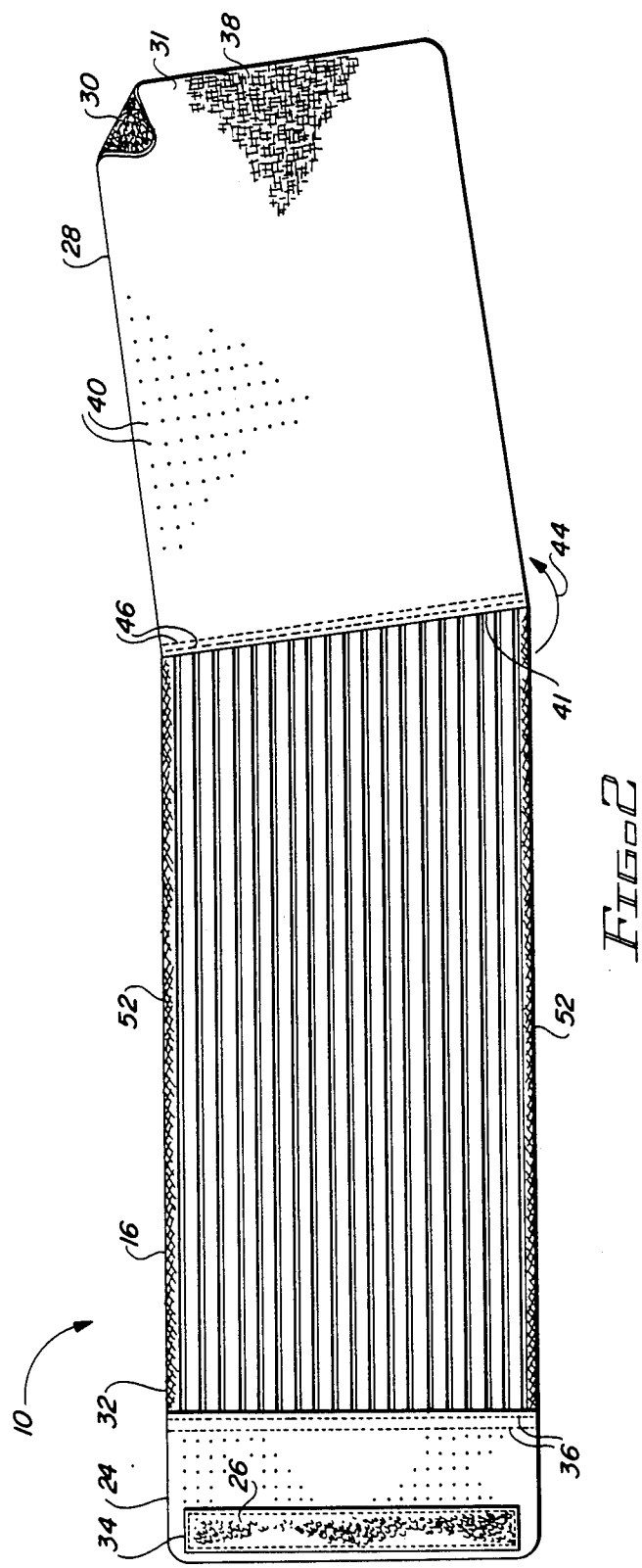

ABDOMINAL BINDER

TECHNICAL FIELD OF THE INVENTION

The present invention relates in general to body wraps, and more particularly relates to a universally adjustable wrap with a unidirectionally stretchable panel through which a wound or suture can be observed.

BACKGROUND OF THE INVENTION

The healing of an abdominal injury or surgical operation can be properly supervised only if frequent inspections of the wound or sutures can be made. The torso of a person, and particularly the abdominal area, must be constrained by a body wrap, or the like, to prevent reopening of the wound or incision. Unless proper support of the wound or incision is provided, the sutured tissue may be pulled or ripped, thus resulting in a reopened wound and possible infection.

Various wraps and abdominal bandages are available for wrapping about a patient and restricting the expansion of the torso so that the wound or incision is constrained. In body wraps with elastic sections, sufficient expansion is provided for allowing the patient to breathe. However, the vertical and lateral stretchable nature of the panel also allows the wound to expand outwardly, thereby placing undue stress on the sutured tissue. A common approach to resolve this problem is the use of surgical tape placed around the wound or incision to prevent tissue stretching in areas localized around the wound. The obvious problem here is that the removal of the tape itself can reinjure the wound. To circumvent this problem, an absorbent gauze or cotton-type material is often taped over the wound. Again, this approach makes frequent inspection of the wound difficult, and moreover, a reinjured or bleeding wound cannot be easily discovered until the absorbent gauze or cotton material has been saturated with body fluids.

It may be seen that a need has arisen for an abdominal wrap or binder which is universally adjustable so as to accommodate a large variety of torso sizes and which is stretchable in the lateral direction only so as to provide improved support. There is a concomitant need for a body wrap with areas through which the wound or surgical incision can be inspected, thereby eliminating the need to remove the wrap.

SUMMARY OF THE INVENTION

In accordance with the present invention, a body wrap is provided which substantially eliminates or reduces the problems associated with the prior art techniques.

In accordance with a feature of the present invention, the body wrap includes a large panel of a unidirectionally stretchable elastic which is laterally stretchable about the patient to allow breathing, but which is nonstretchable in the vertical direction, thereby providing added support to the abdominal wound or incision.

In accordance with another feature of the invention, the unidirectionally stretchable panel includes a plurality of patterned areas through which the wound or incision may be observed. In particular, the stretchable panel is comprised of a plurality of elongate transversely stretchable sections, each connected by vertical monofilament threads spaced apart so that the wound can be seen therethrough. The vertical monofilament threads are nonstretchable and thus prevent the stretching of the panel in the vertical direction.

In accordance with yet another feature of the invention, one side edge of the unidirectionally stretchable panel has attached along the entire edge thereof a Velcro hook-like material. The other side edge of the stretchable panel has attached thereto a large section of a brushed pile material engagable with the Velcro hook material. The Velcro hook material is removably engagable at any location on the large brushed pile section, and thereby accommodates patients of diverse abdominal sizes.

In accordance with a related feature of the invention, all parts of the abdominal binder are constructed of synthetic materials so that the entire article can be fabricated with heat seal bonding techniques, thereby achieving a substantial saving in labor and time in manufacturing the wrap.

BRIEF DESCRIPTION OF THE DRAWINGS

Further features and advantages of the present invention will become apparent from the description of an illustrative embodiment thereof, taken in conjunction with the accompanying drawings, in which:

FIG. 2 is an elevational view of the invention, as viewed from the inside thereof;

DETAILED DESCRIPTION OF THE INVENTION

The present invention is concerned primarily with an abdominal wrap or binder with improved wound or suture support, and which is constructed to provide improved visibility for proper wound management. In addition, the abdominal wrap of the present invention is adjustable over a wide range of abdominal sizes, and is constructed of materials for greatly facilitating the manufacture thereof.

Figure 1:
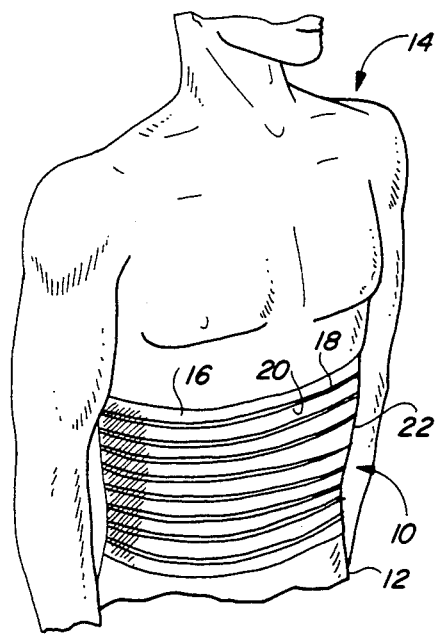
FIG. 1 is a front elevational view of the abdominal wrap according to the invention, secured around the abdomen of a patient.

Turning now to the drawing, there is shown in FIG. 1 a body wrap 10 secured about the abdomen 12 of a patient 14. It should be appreciated, however, that the abdominal wrap 10 can be secured at any location on the torso of the patient 14. The abdominal wrap 10 includes a unidirectionally stretchable panel 16 fabricated for optimum wound maintenance. By this it is meant that the stretchable panel 16 includes means, such as apertured sections 18, through which an incision 20, or the like, can be observed. Alternately interposed between the apertured sections 18 are stretchable support sections 22 for providing lateral support of the abdominal incision 20. As will be described in more detail below, the support sections 22 are connected together by a plurality of vertically oriented filaments which are exposed at the apertured sections 18, and which prevent stretching of the panel 16 in the vertical direction. Not shown in FIG. 1 are pressure responsive attachment means integral with the side edges of the stretchable panel 16 and removably fastened on the back of the torso of the patient 14. It should be understood that the wrap 10 can be secured about the patient 14 at any angular position so that the strechable panel 16 covers the sutured area of the patient.

In FIG. 2 the inside surface of the abdominal wrap 10 is illustrated. As defined herein, the inside of the abdominal wrap 10 is that side surface which contacts the patient. The abdominal wrap 10 comprises a rectangular-shaped unidirectionally stretchable panel 16 with a hook-like material section 24 joined to one side edge thereof. The hook-like material comprises a patch of Velcro hooks 26. At the other side edge of the stretchable panel 16 is a large section 28 with the outside surface fabricated of a pile material brushed into a plurality of loops 30. The hook-like Velcro material 26 is engagable with the brushed loops 30 when pressed thereonto and released when the sections are pulled apart. The composition of the inside surface 31 of the large section 28 will be described fully below.

In the preferred form of the invention, the abdominal wrap 10 is about forty-eight inches long (laterally) and twelve inches wide (vertically). These dimensions may vary depending upon particular applications. In the preferred form of the invention, the large pile section 28 has a lateral dimension of about thirteen inches, and the elastic panel 16 has a corresponding dimension of about thirty two inches. The hook-like fastening section 24 is about three inches by twelve inches and is constructed of a nonwoven polyester material heat seal bonded 32 in a grid pattern on the entire surface thereof. The Velcro hook material 26 is about one and one-half inches by ten inches and is heat sealed bonded 34 around its periphery to the hook-like fastening section 24. It is to be noted that the large pile section 28 is about eight times wider than the hook material 26 width. Substantial lateral adjustability is thus provided. At least a fourfold ratio is preferable. During fabrication of the abdominal binder, the hook-like fastening section 24 is overlapped with and temporarily fastened to the stretchable section 16 with a polyamide adhesive. The hook-like fastening section 24 is then heat seal bonded 36 along its entire side edge to the stretchable panel 16. The polyamide adhesive is obtainable from Samuel Haler's Sons, and is known as Apparel Lock No. 30.

The large brushed pile section 28 of the abdominal wrap 10 is of a laminate construction including a polyester pile material 30 on the outside surface, and a nonwoven polyester 38 on the inside surface 31. The polyester pile material 30 and the nonwoven polyester 38 are heat seal bonded 40 in a grid pattern over the entire surface of the large section 28. The nonwoven polyester 38 is not engagable with the hook-like material 26. As noted in FIG. 2, the hook-like material 26 is located on the opposite side of the abdominal wrap 10 to the brushed pile surface 30. In wrapping the abdominal wrap 10 around a patient, the stretchable panel 16 is first placed against the portion of the patient's torso which is to be secured, then the large brushed pile section 28 and the hook-like fastening section 24 are wrapped around the patient. The nonwoven inside surface 31 of the large section 28 is held against the patient's body with the brushed pile surface 30 disposed outwardly, and then the hook-like fastening section 24 is pulled tightly around the patient and the hook-like material 26 is pressed onto the brushed pile surface 30. With this construction, no loose ends of the wrap 10 are left dangling from the patient. The taughtness of the abdominal binder can be adjusted simply by pulling the engaging hook-like material 26 apart from the brushed pile surface 30 and reengaging the sections together with the desired stretch in the stretchable panel 16.

As noted in FIG. 2, the stretchable panel 16 is cut on a bias 41. The large brushed pile section 28 is attached thereto so that an angle is formed between the stretchable panel 16 and the large brushed pile section 28. This angled nature permits a better alignment of the hook-like section 24 with the large brushed pile section 28 when wrapped around the irregular shaped torso of a person. As with the hook-like section 24, the brushed pile section 28 is temporarily fastened to the stretchable panel 16 by a polyamide adhesive, and then heat seal bonded 46 along the entire overlapping edges thereof to form a permanent and integral structure.

Figure 3:
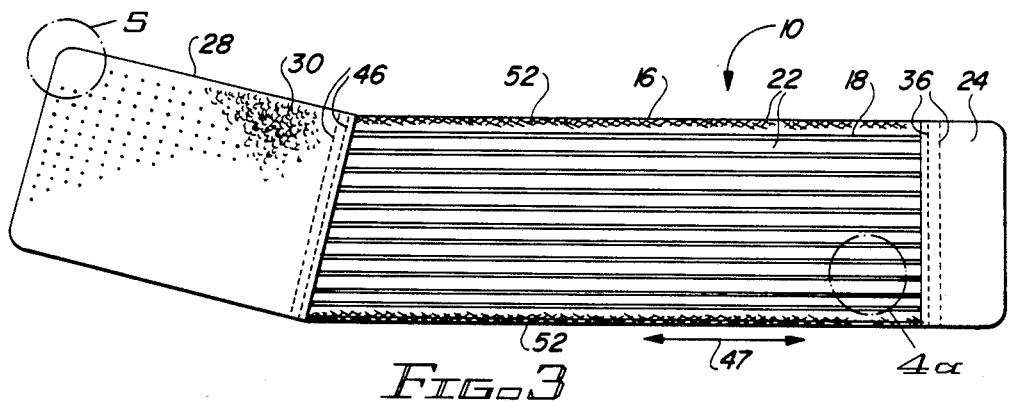
FIG. 3 is a front elevational view of the outer surface of the abdominal wrap.

In FIG. 3 the outer side surface of the abdominal wrap 10 is illustrated. Of particular importance is the characteristic of the stretchable panel 16 which allows it to stretch only in the direction shown by arrow 47. Of equal importance, the stretchable panel 16 includes apertured sections 18 through which the tissue or body of the patient can be observed.

The construction of the stretchable panel 16 is shown in more detail in the enlarged view of FIG. 4. As noted above, interspersed between the stretchable support sections 22 are a plurality of apertured sections 18. In practice, the stretchable panel 16 is constructed so that each stretchable support section 22 is about ¼ inch wide, while the apertured sections 18 are about 1/32 of an inch wide. Thus, in a stretchable panel 16 having a width of about one foot, there are approximately forty-three sections for observing the underlying tissue of the patient. Because of the contrasting color of an incision or wound with respect to the skin color, the wound or incision can be easily observed without removal of the abdominal wrap 10.

Figure 4A:
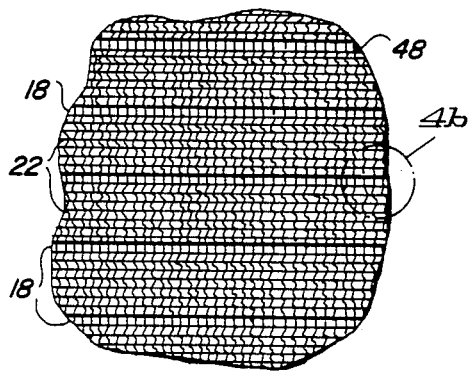
FIGS. 4a and 4b are enlarged views of a portion of the unidirectionally stretchable panel.
Figure 4B:
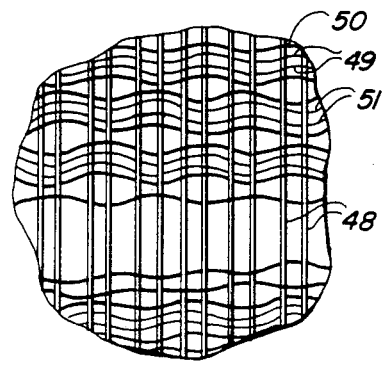

The unidirectionally stretchable elastic is best illustrated in FIGS. 4a and 4b. The nylon strands 48 comprise nylon 148 denier 5.5 mil. Woven with strands 48, and woven in a direction transverse to the strands 48, are various synthetic filler and foundation yarns, and elastic materials. An elastic material 49 is woven with the nylon monofilament strands 48. The elastic material is a composite structure including a polyether spandex 377 denier material, and a textured nylon type 6,6 70/34. Woven to provide body to the stretchable panel 16 are warp yarn textured nylon threads, type 6-6 2/100/34, designated by reference character 50. A third fabric strand 51 is woven together with strands 49 and 50, and is identified as a warp yard textured nylon, type 6,6 2/70/34. Strand 51 operates to lock the nylon strands 48 in place. The pattern of these four strands is repeated. Unidirectional material of the type described can be obtained from the George C. Moore Corp., P.O. Box 1634, Providence, R.I. 02903. The elastic material 49, the warp yarn 50 and support strands 51 are woven around the nylon strands 48 in lateral support sections 22. The nylon strands 48 are not densely packed, but are exposed at apertured areas 18. Thus, the tissue of the torso thereunder can be visually examined through the stretched material without removing the abdominal wrap 10.

With this construction, the stretchable panel 16 provides an improved abdominal support around a wound or incision, but yet allows a certain degree of expansion of a patient's torso for breathing, or for the movement of the upper body. It should be understood that when the stretchable panel 16 is stretched in the direction shown by arrow 47, the nylon strands 48 become more separated, thereby effectively enlarging the apertures and allowing better visibility of the wound or incision 20. Moreover, because the stretchable panel 16 is only unidirectionally expansible, the vertical dimension of the panel 16 does not become narrower when subjected to horizontal stretching, as is customary with multi-directionally stretchable material. The abdomen or torso of the patient is thereby provided with an improved support without the need of stretching the wrap too tightly around the patient. To prevent the unraveling, the elastic panel 16 is cross-stitched 52 along the top and bottom edges thereof.

Figure 5:
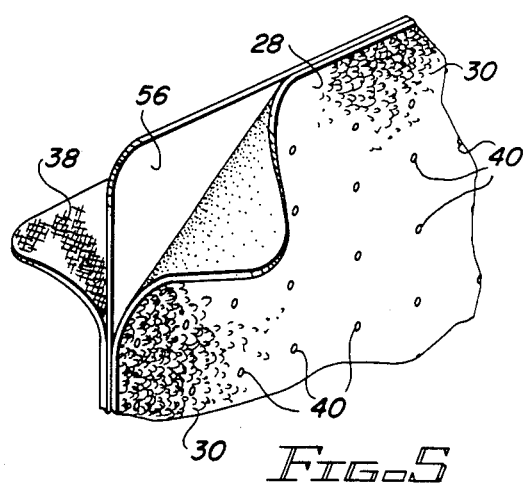
FIG. 5 is a much-enlarged view of a section of the brushed pile pressure responsive engaging pile material.

FIG. 5 is an enlarged view of a portion of the laminated brushed pile section 28. Covering the entire surface of the large brushed pile section 28 are the unbroken loops 30, as noted above. The large brushed pile section 28 includes an outer polyester layer 54 with pile 30, a middle nonwoven polyester filler 56 and an inner surface of the nonwoven polyester 38. All three layers 38, 54 and 56 are heat seal bonded 40 in a ⅛ inch grid over the entire surface of the section 28.

It is to be noted from the above-described construction of the abdominal panel 10, that all the materials thereof are synthetic in nature, and heat seal bondable together to reduce the time and labor needed to assemble the article into a finished integral product.

In summary, there has been provided an abdominal wrap which is undirectionally stretchable to provide improved support around the torso of a patient, and which includes apertured sections through which a wound or suture can be observed. In addition, the abdominal wrap of the invention includes a large engagingly mating section to provide a large degree of adjustability for patients of diverse torso sizes. The present invention is constructed entirely of synthetic materials for ease of cleaning, and more importantly, to facilitate the fabrication thereof to substantially reduce manufacturing costs.

Although the invention has been described above with a certain degree of particularity with respect to the materials and construction thereof, it should be understood that this disclosure has been made only by way of example. Consequently, changes in the details of the construction and in the arrangement of the elements, as well as possible modes of utilization, will become apparent to those familiar with the art, and may be resorted to without departing from the scope of the invention as claimed below.

What is claimed is:

1. A body wrap securable around the body of a person, comprising:

a rectangular shaped stretchable panel section wrappable at least partially around the person for securement thereof, said panel including a plurality of parallel spaced apart nonstretchable filaments extending parallel to the shorter length of said rectangle;

a plurality of elongate spaced apart unidirectionally stretchable sections woven about said filaments and extending transverse to said filaments, said sections alternating with a plurality of parallel elongate spaces, each said nonstretchable filament crossing said spaces, each said space divided into a plurality of rectangular apertures by said filaments, each rectangular aperture unidirectionally stretchable in a direction parallel to the longer length of said rectangle, each rectangular aperture increasing in area when stretched in a direction parallel to the longer length of said rectangle, to allow the observation of parts of said body therebeneath;

a first section integral with one side edge of said panel and including a plurality of loops distributed over one entire surface thereof;

a second section integral with an opposing side edge of said panel and including a plurality of elements engageable with said loops of said first section to thereby fasten said wrap secured in a stretched condition around the person.

2. The body wrap of claim 1 wherein each said nonstretchable monofilament passes through each said space.

3. The body wrap of claim 1 wherein each said space extends substantially the entire longer length of said panel.

4. The body wrap of claim 1 wherein said nonstretchable monofilaments comprise a plurality of substantially parallel nylon filaments, said panel sections each interwoven with said nonstretchable monofilaments substantially transverse thereto and comprising a plurality of (a) strands comprising polyether spandex and textured nylon, (b) strands comprising warp yard textured nylon and (c) strands comprising filling yarn monofil nylon.

5. The body wrap of claim 1 wherein said first section includes an area greater than one square foot having distributed on one surface thereof said loops.

6. The body wrap of claim 1 wherein said first and second sections are each overlapped and bonded to opposing edges of said stretchable panel with an adhesive tape therebetween.

7. The body wrap of claim 1 wherein the loops of said first section and the hook-like elements of said second section are located on opposing side surfaces of said body wrap.

8. The body wrap of claim 1, wherein the length of said one entire surface of said first section greatly exceeds the length of said elements of said second section, such that said elements may be engaged with said surface at any of a plurality of locations on said surface and such that the adjustment of said wrap to the girth of said body is possible.

* * * * *